United States Patent [19]

Melican

[11] 4,232,674
[45] Nov. 11, 1980

[54] LIQUID ABSORPTION DEVICES

[75] Inventor: Nigel J. T. Melican, Goldington, England

[73] Assignee: Lever Brothers Company, New York, N.Y.

[21] Appl. No.: 966,692

[22] Filed: Dec. 5, 1978

Related U.S. Application Data

[63] Continuation of Ser. No. 714,466, Aug. 16, 1976, abandoned.

[30] Foreign Application Priority Data

Aug. 22, 1975 [GB] United Kingdom ............... 34974/75

[51] Int. Cl.³ ............................................. A61F 13/16
[52] U.S. Cl. .................................... 128/287; 128/285
[58] Field of Search ............... 128/156, 284, 285, 287, 128/290, 296; 536/106, 108; 428/236–237, 264

[56] References Cited

U.S. PATENT DOCUMENTS

| | | | |
|---|---|---|---|
| 2,062,978 | 12/1936 | King | 128/287 |
| 2,853,484 | 9/1958 | Lolkema et al. | 536/108 |
| 2,952,260 | 9/1960 | Burgeni | 128/290 R |
| 3,078,849 | 2/1963 | Morse | 128/290 R |
| 3,381,688 | 5/1968 | Satas | 128/290 R |
| 3,441,021 | 4/1969 | Endres | 128/156 |
| 3,622,562 | 11/1971 | Muetgeert | 536/106 |
| 3,670,731 | 6/1972 | Harmon | 128/287 |
| 3,865,112 | 11/1975 | Roeder | 128/284 |
| 3,888,257 | 6/1975 | Cook et al. | 128/296 |
| 3,903,889 | 9/1975 | Torr | 128/287 |
| 4,058,124 | 11/1977 | Yen et al. | 128/284 |
| 4,105,033 | 8/1978 | Chatterjee et al. | 128/285 |

FOREIGN PATENT DOCUMENTS

| | | | |
|---|---|---|---|
| 869206 | 4/1971 | Canada | 128/287 |
| 432825 | 8/1935 | United Kingdom | 128/290 R |
| 549129 | 11/1942 | United Kingdom | 128/290 R |
| 585888 | 2/1947 | United Kingdom | 128/156 |
| 905504 | 9/1962 | United Kingdom | 128/290 R |
| 936039 | 9/1963 | United Kingdom | |
| 1042864 | 9/1966 | United Kingdom | 536/106 |

*Primary Examiner*—C. Fred Rosenbaum
*Attorney, Agent, or Firm*—Michael J. Kelly; James J. Farrell; Melvin H. Kurtz

[57] ABSTRACT

A liquid absorbent device such as a diaper, sanitary towel or tampon includes one or more layers of a material with capillarity and carries an absorbent deposit in a predetermined pattern, for example parallel stripes, to leave uncovered areas for capillary flow of liquid from saturated to unsaturated areas of the layer. The absorbent deposit may be a highly absorbent starch based gel.

17 Claims, 6 Drawing Figures

LIQUID ABSORPTION DEVICES

This is a continuation of application Ser. No. 714,466, filed Aug. 16, 1976, and now abandoned.

The present invention relates to liquid absorbing devices, for example diapers, sanitary towels or tampons or other disposable sanitary products.

Various liquid absorbing devices can be produced as a fibrous base material coated with a highly liquid absorbent material. Such absorbent materials, generally water-swellable gel-forming polymers, for example modified celluloses and cross-linked carboxyalkylated starch derivatives, have the property of absorbing large quantities of liquid, and thus a product can be made of less bulk than hitherto and with the same liquid absorbent properties. This is of particular benefit for disposable diapers, sanitary towels and tampons.

The present invention is concerned with providing a liquid absorbent device of this type where the super absorbing properties of the gel can be made use of even more effectively than hitherto. We have appreciated that while such gels enable greater quantities of liquid to be absorbed, the rate at which such liquid is absorbed needs to be improved as well, and that this can be best achieved by making a more effective use of the total area on which, or volume within which, the absorbent gel is carried.

Thus, the present invention provides a liquid absorbent device comprising at least one layer having capillarity and carrying a deposit of absorbent material in a pre-determined pattern which leaves areas without absorbent deposit but with capillarity, for the flow of liquid from saturated to unsaturated absorbent areas. Thus, in use liquid to be absorbed can be carried by capillarity from say a central area to outlying areas of the pad to be absorbed by the absorbent deposit in areas which would otherwise not be completely used.

A further advantage is that the absorbent deposit will have a finite rate of fluid absorption, and fluid can be temporaily stored in the absorbent-free areas until the deposit is capable of receiving more fluid, i.e. these areas act as temporary reservoirs.

The absorbent deposit will be selected to have a desired high rate or capacity for absorption, and may thus be one of the previously mentioned gel-forming materials. It has been found however that gels based on non-fibrous starting materials (in particular starches rather than cellulosic materials) an additional benefit occurs in the increased wicking that takes place.

Preferably the pattern is in the form of stripes, desirably parallel, so as to leave channels between the stripes along and within which the liquid can flow. Flow is primarily capillary to start with but as the gel swells larger channels are defined. This enables directional spreadability and absorption to be achieved. Then with an oblong article such as a sanitary towel, the stripes can be arranged longitudinally and will cause flow of liquid longitudinally on the article to absorbent deposit at the extremities of that article. This effect can also be made use of in a tampon, for getting liquid from the outside into the centre.

In the case of an article having a plurality of layers, which are superimposed, the product according to the invention has an added advantage that where in a continuous layer saturation would block transmission of liquid from the first layer to subsequent layers (blinding), by leaving areas without absorbent deposit a passageway will be obtained as between the first layer and subsequent layers even in the case of saturation. This penetration can be further enhanced by providing fine perforations in the areas without absorbent deposit.

While sometimes difficult to achieve in practice, it is desirable that the stripes of adjacent layers are co-planar. This results in a more clearly defined passageway to successive layers.

In the case of a sanitary towel, below (in the sense of the directional travel of liquid from the first or upper side) the patterned layers it is preferable to have a continuous deposit absorbent layer. This acts as a final shield and buffer zone from which surplus liquid can spread back into the patterned layers. Preferably this continuous deposit layer should shield the edges of the superposed patterned layers.

Below the continuous deposit layer should be an impervious layer, for example of polyethylene.

The absorbent deposit is preferably a highly liquid-absorbent gel-forming polymer, for example a cross-linked carboxyalkylated starch derivative. Such materials may be applied to the, or each backing layer of material with capillarity by application of a dry powder followed by a steam treatment. The preparation of such materials is described in our co-pending applications 58 916/73, 58 917/73 and 31 672/73.

Three embodiments of the invention will now be described by way of example with reference to the accompanying diagrammatic drawings in which FIG. 1 shows an apparatus for applying stripes of absorbent deposit to a carrier layer;

Figure 1:
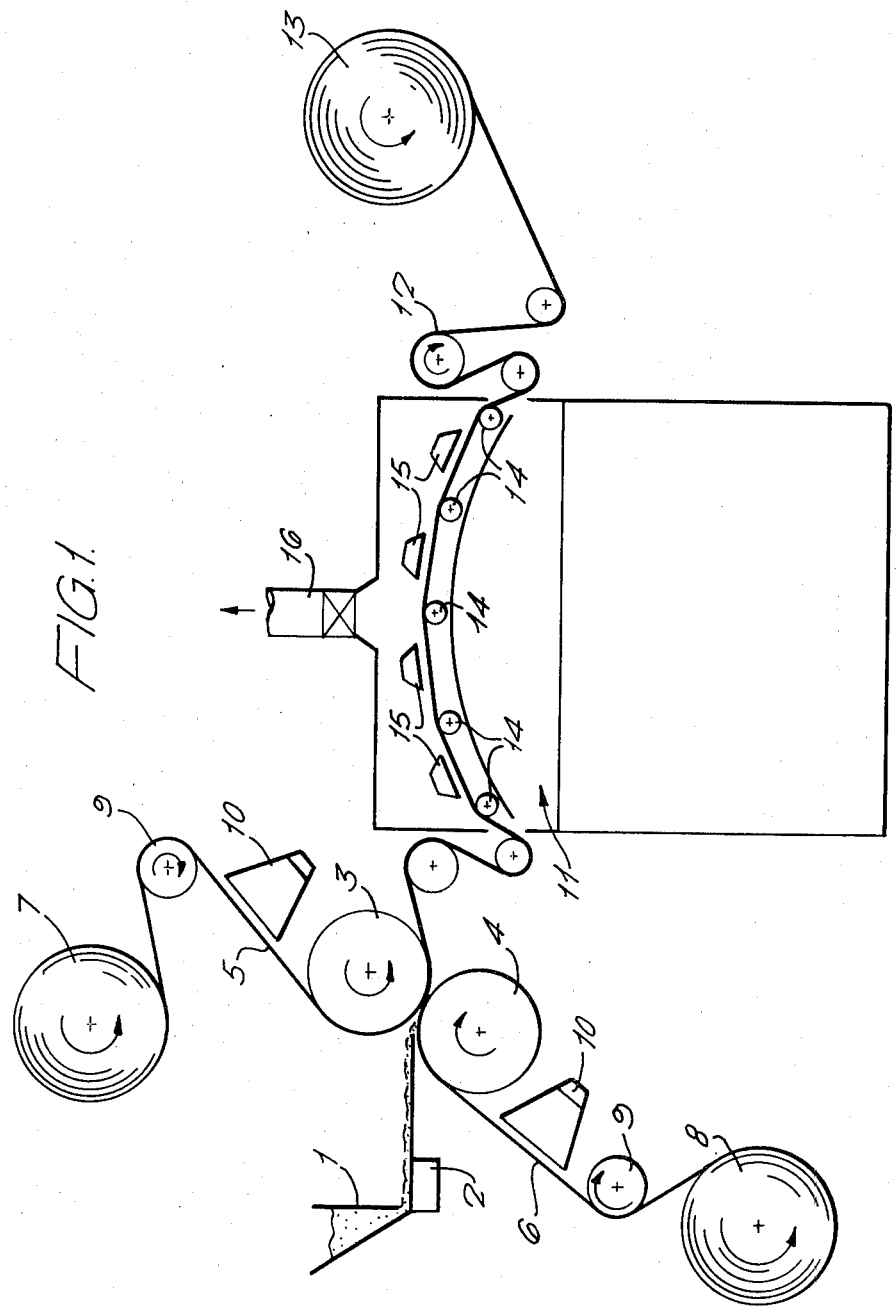

A suitable absorbent starch derivative is one in which cross-linking has been achieved by the reaction of starch in an alkaline medium with a chloroalkyl oxirane, particularly epichlorhydrin, and the derivative is preferably one derived by replacement of a proportion (suitably in the range 0.1 to 0.8:1) of the hydroxyl groups of such crosslinked material with a carboxyalkyl group, particularly carboxymethyl. A suitable derivative is one obtained as follows:

1000 g of potato starch was slurried in 950 ml of water containing 10 g of epichlorhydrin. 5 g of sodium hydroxide in 50 ml of water was added with stirring and the mixture was applied to a roller heated by steam at 40 lb/sq in gauge (180° C.). The cross-linked starch derivative was removed from the roller as flake and passed through a 2.0 mm screen.

100 g of this cross-linked starch was put in a mixer and sprayed with a solution of sodium hydroxide (34 g) in water (66 ml) followed by a solution of monochloracetic acid (39 g) in water (11 ml). After ageing overnight in a polythene bag the product (theoretical degree of substitution 0.67) was slurried in hydrochloric acid (N; 2000 ml). The product was filtered and washed with 5×2000 ml quantities of water. Ammonia solution (50 ml; specific gravity 0.88) was added with stirring to the final filter cake. The product was air dried and milled through a 0.8 mm screen. 1 g of the powder absorbed 29 ml of water yet remained dry to the touch.

Referring to FIG. 1 a hopper 1 contains the highly absorbent milled particulate cross-linked carboxyalkylated starch derivative gel. A vibratory feeder 2 with a series of grooved channels is arranged to feed this gel material as a number of parallel lines of powder into the nip of a pair of rollers 3, 4 of which the upper roller 3 is of steel and the lower roller 4 of rubber so as to accommodate variations in the size or evenness of the particle layer.

Also feeding into the nip of the rollers 3, 4 are two layers of tissue carrier material 5, 6 supplied from supply rolls 7, 8 via intermediate feed rollers 9. In each case a water spray device 10 is provided which wets the tissue carrier webs 5 and 6 before they reach the nip of rollers 3 and 4.

The wetted carrier layers 3, 4 then receive the parallel rows of particulate gel at the nip of the two rollers 3 and 4 and thereafter feed forward as a composite sandwich ply incorporating these rows as parallel stripes through a heating chamber 11 which removes moisture from the tissue carriers and gel, round a cooling roller 12 and thence to a storage reel 13.

The heating chamber 11 is an enclosure consisting essentially of an open feedthrough system of rollers 14, radiant heaters 15, and forced extraction exhaust duct 16.

Figure 2:
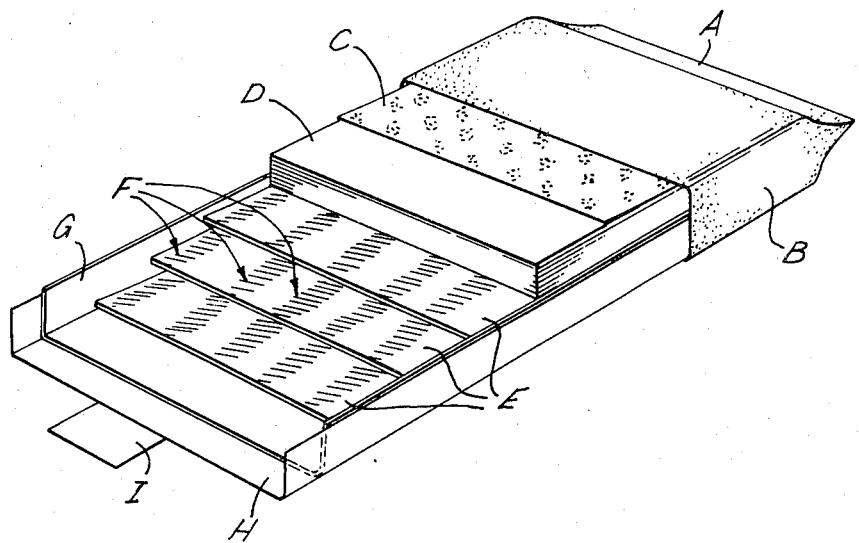
FIG. 2 shows a first form of sanitary towel.

The towel shown in FIG. 2 consists of a non-woven longitudinal layer rayon fabric outer wrapper B, which should be water-soluble. This wrapper is transversely sealed at its ends A.

Immediately below the wrapper is a stain reducing layer C. This is desirably a silicone-treated perforated nonwoven layer. The product sold by Johnson & Johnson under the name "Babydry" is suitable.

Below the stain-reducing layer is a penetration layer D consisting of 16 layers of multiply crepe of 26 grammes per square meter weight. Then below the penetration layer are three layers of striped absorbent polymer-coated sandwich material E.

Each layer consists of two sandwiched sheets of crepe tissue E, which is a basically non-absorbent material having a structure which causes capillary flow of liquid along that layer. As a deposit in that layer E are a series of stripes F of the cross-linked carboxylated starch derivative.

As previously described the absorbent deposit is applied as stripes F by applying lines of powder to the carrier material in the presence of water and then applying pressure. The stripes are 4 mm wide with a 4 mm spacing between each. The material is applied to the centre of the sandwich at a rate of 70 grammes per square meter of total tissue area.

Around the three layers E is a lower absorbent sheet G, which consists of a crepe tissue carrier layer carrying a continuous deposit of the absorbent material. This serves as a moisture barrier, particularly at the edges of the striped layers E.

Then finally below the absorbent moisture barrier G is an impervious polyethylene layer H, and on the outside a gripstrip keeper I which is a conventional silicone treated adhesive tape for keeping the towel in position in use.

Figure 3:
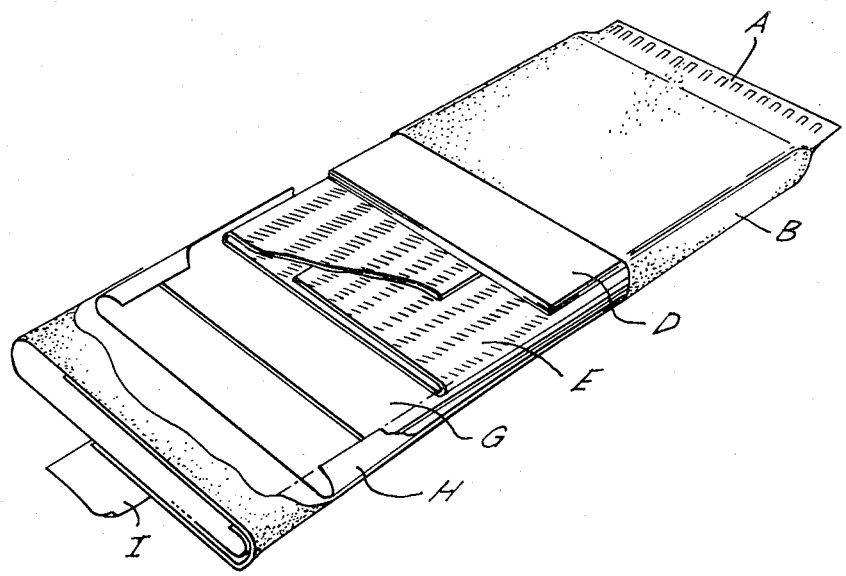
FIGS. 3 and 4 show a second form of sanitary towel.
Figure 4:
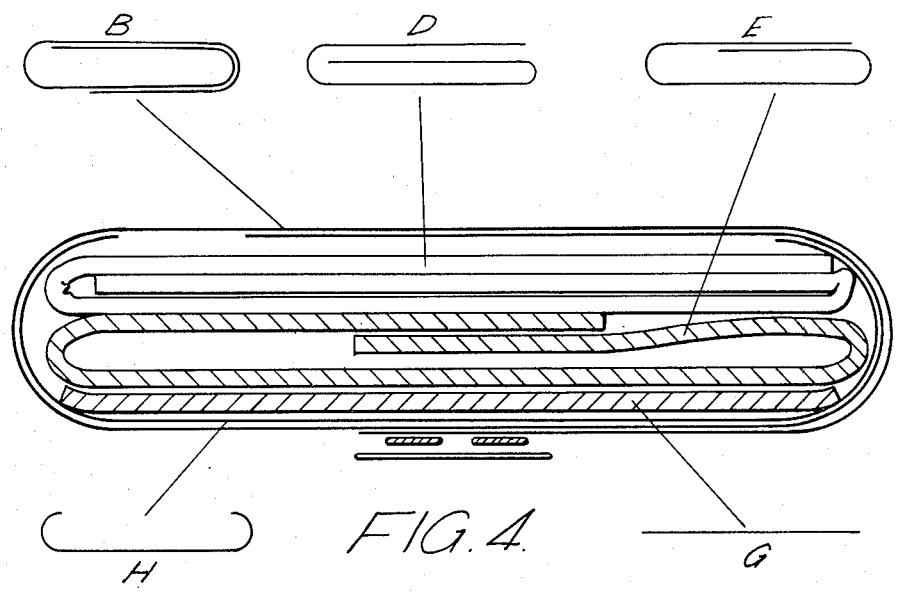

A second embodiment will now be described with reference to FIGS. 3 and 4.

The basic format was the same and the same reference numerals are used. However the non-stain layer C was omitted and the various sandwich layers were made by folding of a larger sheet of sandwich material as shown in the appended diagrams of FIG. 4. The Table below specifies the materials used.

Figure 5:
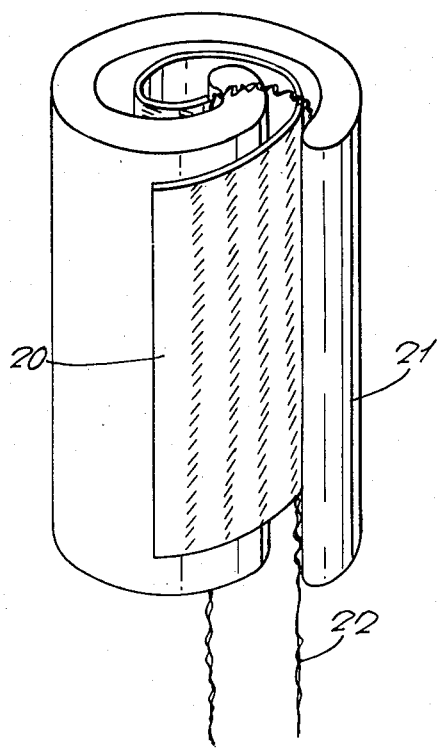
FIGS. 5 and 6 show a tampon.
Figure 6:
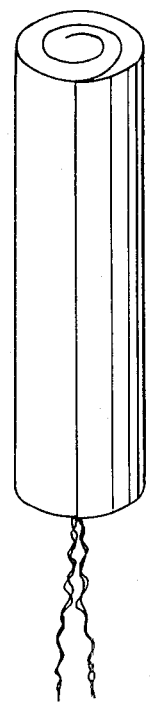

Finally FIGS. 5 and 6 show a tampon formed from a rolled sheet 20 of the gel sandwich material interspersed with a layer 21 of a long staple fibrous material of cotton, rayon or a cotton/rayon mix. A withdrawal cord 22 is provided.

TABLE

| | | | | | |
|---|---|---|---|---|---|
| B | Non-woven wrapper | Water-dispersible | PRK 45 | Bonded fibre fabrics | 260 × 215 mm |
| D | Crepe Penetration layer | Bleached wadding | 5-ply | Charles Turner Ltd | 185 × 195 mm |
| H | Polythene film | Opaque white | 5 micron | 4P Folie Forchheim GmbH | 80 × 215 mm |
| | Adhesive | Hot melt: pressure-sensitive | Lunatack 56 | Industrial waxes | 0.3 g |
| I | Keeper | Silicone treated paper | 42'112 | Jointine | 19 × 215 mm |

What is claimed is:

1. A liquid absorbent device comprising: an absorbent layer, said absorbent layer consisting of:
   (a) at least one carrier sheet of substantially non-absorbent material, wherein said material causes capillary flow of a liquid along said sheet when said sheet is contacted with said liquid; carrying
   (b) a deposit of absorbent materials applied to said carrier sheet in a predetermined pattern of stripes; wherein said stripes leave uncovered areas of said carrier sheet thereby providing channels for said capillary flow of said liquid from saturated to unsaturated areas of said absorbent material.

2. A liquid absorbent device according to claim 1 wherein said absorbent material is a highly absorbent water swellable gel-forming polymer.

3. A liquid absorbent device according to claim 2 wherein said polymer is in the form of non-fibrous particles.

4. A liquid absorbent device according to claim 2 wherein said polymer is a cross-linked carboxyalkylated starch derivative.

5. A liquid absorbent device according to claim 1, wherein said layer is oblong and wherein said stripes are arranged longitudinally to said layer.

6. A liquid absorbent device according to claim 1, having a plurality of said layers.

7. A liquid absorbent device according to claim 6, wherein said plurality of layers are superimposed.

8. A liquid absorbent device according to claim 7, wherein said plurality of layers are formed by folding a single layer.

9. A liquid absorbent device according to claim 8, wherein said layer comprises two sheets of said non-absorbent material and wherein said deposit is sandwiched therebetween.

10. A liquid absorbent device according to claim 9, wherein said device is a sanitary towel.

11. A liquid absorbent device according to claim 10, further comprising a layer comprising a continuous deposit of said absorbent material.

12. A liquid absorbent device according to claim 11, further comprising an impervious layer.

13. A liquid absorbent device according to claim 7, wherein said plurality of layers are formed by rolling a single layer.

14. A liquid absorbent device according to claim 13, wherein said layer comprises two sheets of said non-absorbent material and wherein said deposit is sandwiched therebetween.

15. A liquid absorbent device according to claim 14, wherein said device is a tampon.

16. A sanitary towel comprising:
  (a) a first absorbant member comprising a plurality of layers formed by folding a single layer wherein said single layer consists of:
    (i) two sheets of a substantially non-absorbent material wherein said material causes capillary flow of a liquid along said sheets when said sheets are contacted with liquid; and
    (ii) a deposit of non-fibrous particles of a cross-linked carboxyolated starch derivative in a predetermined pattern of stripes sandwiched between said sheets,
  wherein said stripes provide channels for said capillary flow to said liquid from saturated to unsaturated areas of said absorbent material;
  (b) a second absorbent member comprising a continuous deposit layer of absorbent material wherein said second absorbent member is adjacent to said first absorbent member; and
  (c) a non-absorbent member comprising a layer impervious to liquid, said non-absorbent member being adjacent to said second absorbent member.

17. A sanitary towel according to claim 16, wherein said impervious layer is polyethylene.

* * * * *